(12) United States Patent
Shen et al.

(10) Patent No.: US 9,395,173 B2
(45) Date of Patent: Jul. 19, 2016

(54) MULTI-FUNCTIONED OPTICAL MEASUREMENT DEVICE AND METHOD FOR OPTICALLY MEASURING A PLURALITY OF PARAMETERS

(71) Applicant: NATIONAL APPLIED RESEARCH LABORATORIES, Taipei (TW)

(72) Inventors: Ming-Hsing Shen, Taipei (TW); Wei-Chung Wang, Taipei (TW); Chi-Hung Huang, Taipei (TW); Jyh-Rou Sze, Taipei (TW); Chun-Li Chang, Taipei (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 99 days.

(21) Appl. No.: 14/521,440

(22) Filed: Oct. 22, 2014

(65) Prior Publication Data
US 2016/0116271 A1    Apr. 28, 2016

(51) Int. Cl.
*G01B 9/02* (2006.01)
*G01J 3/45* (2006.01)
*G01J 3/447* (2006.01)

(52) U.S. Cl.
CPC ........ *G01B 9/02042* (2013.01); *G01B 9/02044* (2013.01); *G01J 3/447* (2013.01); *G01J 3/45* (2013.01)

(58) Field of Classification Search
CPC ........... G01B 11/0675; G01B 11/2441; G01B 9/02029; G01B 9/0203
USPC ................................. 356/491, 495, 503, 511
See application file for complete search history.

(56) References Cited

U.S. PATENT DOCUMENTS

| | | | | |
|---|---|---|---|---|
| 4,818,110 | A * | 4/1989 | Davidson | G01B 11/024 356/512 |
| 7,095,507 | B1 * | 8/2006 | Hwang | G01N 21/95607 356/511 |
| 8,416,399 | B2 | 4/2013 | Straehle et al. | |
| 8,416,491 | B2 | 4/2013 | Chen et al. | |
| 2007/0035744 | A1 * | 2/2007 | Lehmann | G01B 11/2441 356/512 |
| 2012/0218561 | A1 | 8/2012 | Ohtsuka et al. | |
| 2013/0033698 | A1 | 2/2013 | Fujimori | |

FOREIGN PATENT DOCUMENTS

TW        096147071       12/1996

* cited by examiner

*Primary Examiner* — Jonathan Hansen
(74) *Attorney, Agent, or Firm* — Chih Feng Yeh; Huntington IP Consulting Co., Ltd.

(57) ABSTRACT

The conventional white-light interferometer, confocal microscope, and ellipsometer are integrated as one device set in a functional sense, and the geometrical parameters conventionally measured may be deduced on the integrated device. Thus, the advantages and efficacies of equipment cost saving, on-line measuring, rapid monitoring, reduced manufacturing time, and reduced possibility of object damage during the manufacturing process may be secured, compared with the prior art.

16 Claims, 5 Drawing Sheets

MULTI-FUNCTIONED OPTICAL MEASUREMENT DEVICE AND METHOD FOR OPTICALLY MEASURING A PLURALITY OF PARAMETERS

BACKGROUND OF RELATED ART

1. Technical Field

The present invention relates to an optically measurement device and an optically measuring method, and particularly to a multi-functioned optically measurement device for measuring a plurality of parameters of an object and a method for optically measuring a plurality of parameters of an object, the parameters may be a surface profile, a gray-level image and a full focal colorful image, and a thin-film thickness.

2. Related Art

With rapid improvement of various micro-level manufacturing technologies in the industry, there is an increasing demand on measurement of such micro-level devices. The various 3D contour measuring technologies used in the prior art can not satisfy with the general requirement any more.

In the semiconductor, flat displays, and micro-electromechanical devices and electronic package fields, since there is a crucial effect of the precision and mechanical property of the surface profile of the micro-structure surface on the product's efficacy and lifetime, the quality presented on the manufacturing process has to be monitored. Hence, there is quite a need to accurately measure the surface profile of the micro-structure, and which is typically done by some optical instruments together with some optical technologies.

How the interferometry, confocal microscopy and ellipsometry functions are performed by the white-light interferometer, microscope, and ellipsometer have been readily known by those persons skilled in the art. They may each deduce a corresponding parameter of a measured object by its optical measurement for monitoring the on-line manufactured semiconductor products.

The interferometer for surface profile measurement of the object is implemented into an optical path. There are three type of interferometers: Mirau, Linnik, and Michelson. For the Mirau and Michelson types, their reference surface is integrated into an object lens and not adjustable. On the other hand, the optical architecture of the Linnik type enables its reference optical-path and optical system to be adjustable and flexible, and which may be manual operated by the user.

A typical commercial confocal microscope may be used to obtain an on-focus whole-field image of a measured object by first vertically scanning the measured object and assembling the scanned images together with an image processing, to obtain a high frequency information for each of the pixels in the scanned image, so that a depth-of-focus gray level of each of the pixels is deduced and thus the whole-field information is secured.

To measure a thin-film thickness, the ellipsometer is generally adopted, in which a linear polarized light is first formed by polarizing a light source, and then adjusted for its phase through a compensation plate. Then, the formed light is incident onto an object having a thin film thereon and then reflected back onto a second polarization plate, an analyzer, and compensated therein. And, a detector is used to record the reflected light and analyze the associated Stokes parameter, and the amplitude and the phase of the reflected light, thereby reversely deducing a thickness information of the thin film.

However, the currently available interferometer, confocal microscope and ellipsometer each only have one single measurement function. And, so far, the efforts on these instruments have been mostly only made for enhanced precision and stability of their measurement algorithms.

In measuring a bulk dimension, a public US patent application, US2013/0033698 A1, disclosed such a method by reflecting two light beams from the front and rare surface of the measured object, detecting a spectrum of the light beams reflected from the front and rare surface of the measured object, respectively, and utilizing a processor to analyze a thickness value between the two faces.

A public US patent application, US2012/0218561 A1, disclosed a method for deducing a bulk dimension by measuring a time difference between light beams are reflected from the front surface and the film interface of the measured object by using a spectrometer or a light detector, i.e. the time difference between the time when a surface reflected light and an interface reflected light are respectively received, and then deducing the bulk dimension by using a computer.

U.S. Pat. No. 8,416,491 B2, disclosed a method capable of on-line recognizes a surface profile of a measured object by employing the confocal microscopy principle, where a series of strip structured light beams are propagating from a light source to explore a depth response curve, so as to secure a depth distribution within a measuring range of the object and thus the surface profile of the measured object may be reversely deduced.

U.S. Pat. No. 8,416,399 B2, disclosed a method for measuring the surface profile and the thickness of the measured object by using a white-light interferometry method and a reverse measurement method.

TW patent, TW096147071, disclosed a method for obtaining a three dimensional contour of a measured object by receiving R, G and B interference signal spectra by using an off-axis digital full color method, and finally calculating three colors, R, G and B, information and phases by using a computer calculation.

However, since the semiconductor industry has a trend to seek a higher integration solution for its manufacturing to achieve a reduced manufacturing time and systematic performance, to further save its manufacturing cost and simplified process flow, the currently used optical measurement devices have a need to be further reduced in its cost and processing time when parameters measurement of the measured object is considered. Moreover, the object stands some possibility of damage when it is moved for the parameters measurement Therefore, how may the optical measurement achieves in an on-line performance becomes an issue to be overcome in the micro-level industries, such as the semiconductor industry.

In view of the above prior arts, it may be known that the optical measurement instruments has a need to get more integrated, so that the efficacies of equipment cost saving, on-line measuring, rapid monitoring, reduced manufacturing time, and reduced possibility of object damage during the product manufacturing process may be achieved to facilitate industry improvement.

SUMMARY

It is, therefore, an object of the present invention to provide a multi-functioned optical measurement device for measuring a plurality of parameters of an object and a method for measuring a plurality of parameters to provide a multi-parameter measurement.

In accordance with the present invention, the multi-functioned optical measurement device for measuring a plurality of parameters of an object comprises a light source unit, comprising an external light source; a collimation unit, coupling the external light source to provide a collimated reference light and a collimated subject light; and a polarizer unit, polarizing the collimated reference light and the collimated subject light, to obtain a polarized reference light and a polarized subject light, the polarized reference light propagating on a propagating path; an aperture unit, comprising a reference light aperture, controlling a light flux of the polarized reference light, having an open and close states, and closing the propagating path of the polarized reference light when the close state is acted; an incident light aperture, controlling a light flux of the polarized subject light; and a measured light aperture; a light splitting unit, diving the polarized light into the reference light and the polarized subject light and coupling the reference light and the polarized subject light onto a first path and a second path, respectively; a measured end unit, locating on the second path, receiving and focusing the polarized subject light to the measured object, the measured object reflecting the polarized subject light passing the light-splitting unit to generate a measured light, the measured light being reflected onto a third path reverse to the second path; a reference light processing unit, locating on the first path, and reflecting the polarized reference light to generate a collimated effect reference light onto the third path when the reference light aperture is at the open state and the optical measurement device is on an interferometer mode and the measured light and the collimated effect reference light jointly generate an interference image through the light-splitting unit, and generating a guided measured image on the third path when the reference light aperture is at the close state and the optical measurement device is on a microscope mode; a spectrum obtaining/image acquiring unit, comprising a polarized light splitting unit, guiding the interference image on the interferometer mode and guiding the measured image on the microscope mode to obtain a first to-be-analyzed image and a second to-be-analyzed image; a spectrum obtaining unit, receiving the first to-be-analyzed image to generate a spectrum data; and an image acquiring unit, receiving the second to-be-analyzed image; and a control-processing unit, performing steps of controlling the measured object to move along a vertical direction on the interferometer mode, and analyzing the second to-be-analyzed image, thereby securing a zero optical path difference for each of a plurality of pixels in the second to-be-analyzed image and recording the zero optical path difference for each of the plurality of pixels in the second to-be-analyzed image, thereby enabling the spectrum obtaining unit to obtain the spectrum data, thereby calculating a surface topography of the measured object according to at least one of the spectrum data and the second to-be-analyzed image; closing the reference light aperture to enable the optical measurement device to enter the microscope mode, enabling the spectrum obtaining unit to obtain the spectrum data when the zero optical path difference exists, activating the measured object to move along the vertical direction, analyzing a focal information of each of the plurality of pixels in the second to-be-analyzed image to obtain a full focal colorful image and a full focal gray-level image, and establishing a depth response curve; activating the measured object to move laterally, to obtain a large-range surface profile according to the spectrum data, the depth response curve and an axial dispersion extent; and deducing a thin-film thickness and an another surface profile according to the spectrum data when the zero optical path difference face exists, when the measured object is a substrate having a coating layer thereon, wherein the surface profile is the another surface profile and the control-processing unit selects to only calculate and present one of the surface profile and the another surface profile. In accordance with the present invention, the method for optically measuring a plurality of parameters of an object comprises steps of (a) providing a collimated reference light and a collimated subject light; (b) polarizing the collimated reference light and the collimated subject light, to obtain a polarized reference light and a polarized subject light, the polarized reference light having a propagating path; (c) controlling a light flux of the polarized reference light, having an open and close states, and closing the propagating path of the polarized reference light when the close state is acted; (d) controlling a light flux of the polarized subject light; (e) diving the polarized light into the reference light and the polarized subject light and coupling the reference light and the polarized subject light onto a first path and a second path, respectively; (f) receiving and focusing the polarized subject light to the measured object, the measured object reflecting the polarized subject light passing the light-splitting unit to generate a measured light, the measured light being reflected onto a third path reverse to the second path; (g) reflecting the polarized reference light to generate a collimated effect reference light onto the third path when the reference light aperture is at the open state and the optical measurement device is on an interferometer mode and the measured light and the collimated effect reference light jointly generate an interference image and generating a guided measured image on the third path when the reference light aperture is at the close state and the optical measurement device is on a microscope mode; (h) guiding the interference image on the interferometer mode and guiding the measured image on the microscope mode to obtain a first to-be-analyzed image and a second to-be-analyzed image; (i) receiving the first to-be-analyzed image to generate a spectrum data and receiving the second to-be-analyzed image; (j) controlling the measured object to move along a vertical direction on the interferometer mode, and analyzing the second to-be-analyzed image, thereby securing a zero optical path difference for each of a plurality of pixels in the second to-be-analyzed image and recording the zero optical path difference for each of the plurality of pixels in the second to-be-analyzed image, thereby enabling the spectrum obtaining unit to obtain the spectrum data, thereby calculating a surface topography of the measured object according to at least one of the spectrum data and the second to-be-analyzed image; (k) closing the reference light aperture to enable the optical measurement device to enter the microscope mode, enabling the spectrum obtaining unit to obtain the spectrum data when the zero optical path difference exists; (l) activating the measured object to move along the vertical direction, analyzing a focal information of each of the plurality of pixels in the second to-be-analyzed image to obtain a full focal colorful image and a full focal gray-level image, and establishing a depth response curve; (m) activating the measured object to move laterally, to obtain a large-range surface profile according to the spectrum data, the depth response curve and an axial dispersion extent; and (n) deducing a thin-film thickness and an another surface profile according to the spectrum data when the zero optical path difference face exists, when the measured object is a substrate having a coating layer thereon, wherein the surface profile is the another surface profile and the control-processing unit selects to only calculate and present one of the surface profile and the another surface profile.

By means of the optical measurement device and method of the present invention, since the traditional white-light interferometer, confocal microscope, and ellipsometer are integrated as one device set in a functional sense, the advantages and efficacies of equipment cost saving, on-line measuring, rapid monitoring, reduced manufacturing time, and reduced possibility of object damage during the manufacturing process may be secured.

BRIEF DESCRIPTION OF THE DRAWINGS

The present invention will be better understood from the following detailed descriptions of the preferred embodiments according to the present invention, taken in conjunction with the accompanying drawings, in which.

DETAILED DESCRIPTION

The present invention will be apparent from the following detailed description, which proceeds with reference to the accompanying drawings, wherein the same references relate to the same elements.

Figure 1:
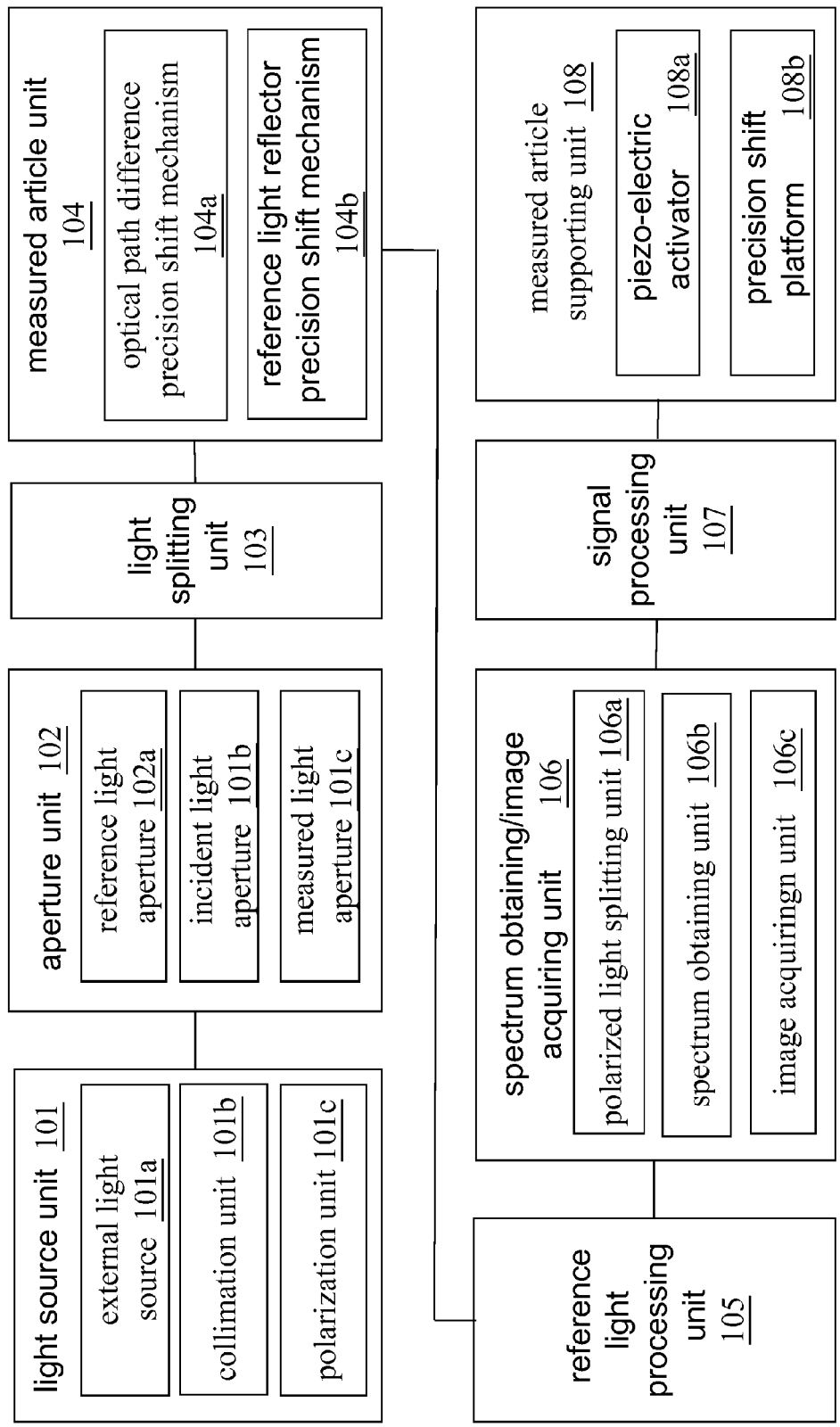
FIG. 1 is a schematic block diagram of multi-functioned optical measurement device for measuring a plurality of parameters of an object according to the present invention.
Figure 2:
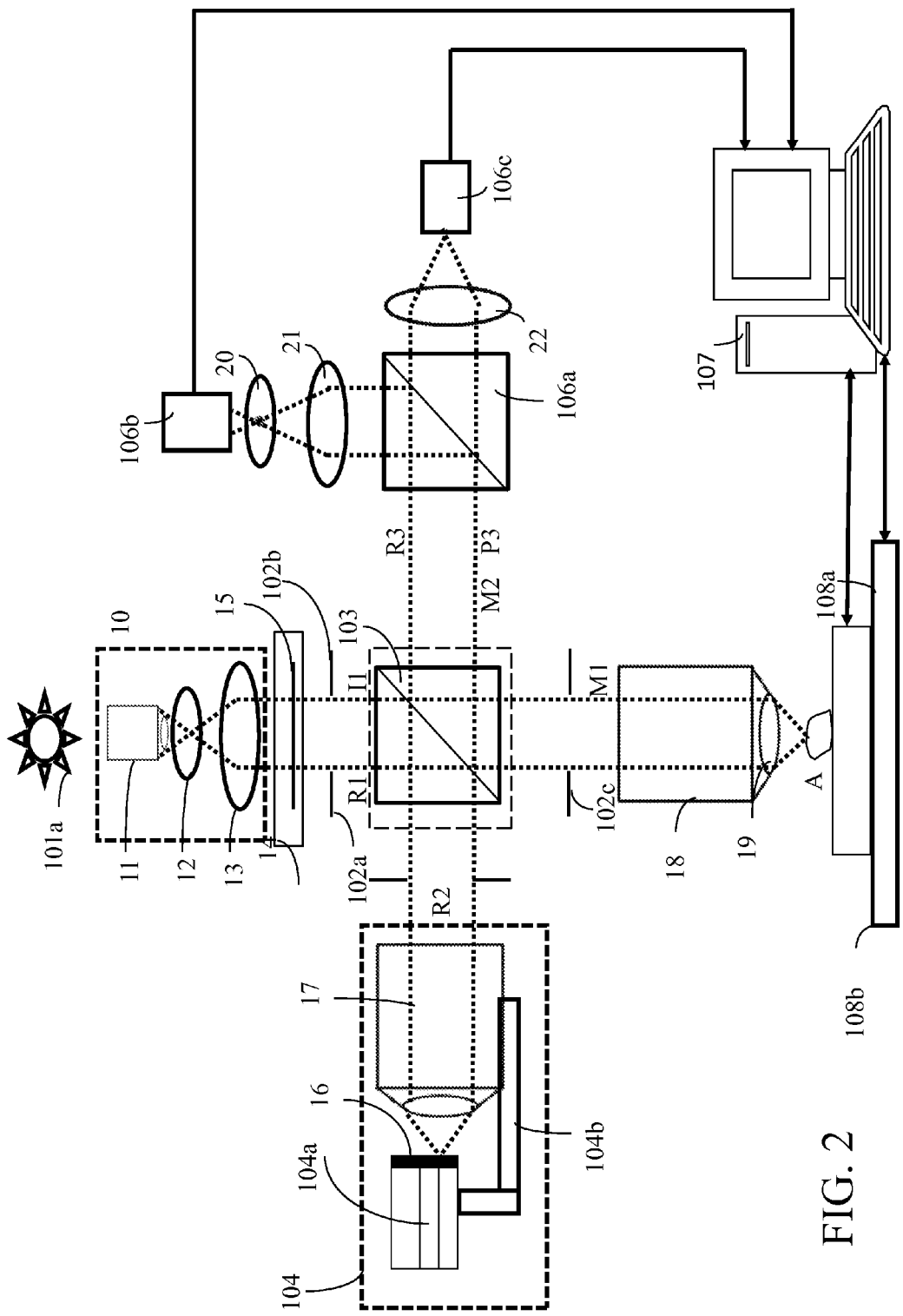
FIG. 2 is a schematic diagram of a further detailed architecture of the multi-functioned optical measurement device for measuring a plurality of parameters of an object according to the present invention.

The present invention sets forth a multi-functioned optical measurement device for a plurality of parameters of an object and a method for optically measuring a plurality of parameters of an object. At first, FIG. 1 and FIG. 2 are used to described the optical measurement device part of the present invention, in which FIG. 1 is a schematic block diagram of a multi-functioned optical measurement device for a plurality of parameters of an object according to the present invention, and FIG. 2 is a schematic diagram of a further detailed architecture of the multi-functioned optical measurement device for a plurality of parameters of an object according to the present invention.

As shown, the optical measurement device 100 comprises a light source unit 101, an aperture unit 120, a beam splitting unit 103, a measured object unit 104, a reference light processing unit 105, a polarization and splitting unit 106, a spectrum obtaining/image acquiring unit 107, and a signal processing unit 107. The optical measurement device 100 is used to measure geometrical parameters of a measured object A, where the measured object A is an object having a substrate with a coating layer thereon, and typically a micro-device such as a semiconductor device.

The light source unit 101 comprises an external light source 101a, a collimation unit 101b, and a polarization unit 101c. The external light source 101 may be a white-light halogen lamp or an infrared lamp, and has a Gaussian intensity distribution. The polarization unit 101c receives the external light source 101a for providing a collimated reference light R1 and a collimated subject light I1. The polarization unit 101c is used to polarize the collimated reference light R1 and the collimated subject light I1, to obtain a polarized reference light R2 and a polarized subject light I2.

The aperture unit 102 comprises a reference light aperture 102a, an incident light aperture 102b, and a measured light aperture 102c. The reference light aperture 102a controls a passing amount of the polarized reference light R2 and has an open and close states. Further, when the close state exists, the reference light aperture 102a closes the propagating path of the polarized reference light R2.

The incident light aperture 102b controls a passing amount of the polarized subject light I2. In addition, the measured light aperture 102c will be explained in the following.

The light splitting unit 103 guides the polarized reference light R2 and the polarized subject light I2 onto a first path P1 and a second path P2.

The measured end unit 104 is located on the second path P2, and receives and focuses the polarized subject light I2 passing the light splitting unit 103 to the measured object A. Then, the measured object A reflects the polarized subject light I2 passing the light-splitting unit 103 to generate a measured light M1, wherein the measured light M1 is reflected onto a third path P3 reverse to the second path P2.

The reference light processing unit 105 is located on the first path P1, and when the reference light aperture 102a is at the open state and the optical measurement device 100 is on an interference mode, it reflects the polarized reference light R2 to generate a collimated effect reference light R3 onto the third path P3. The measured light M1 and the collimated effect reference light R3 jointly generate an interference image through the light-splitting unit 103. The interferometer mode refers to a state when the optical measurement device 100 operates at this time. When the reference light aperture 102a is at the close state and the optical measurement device 100 is on a microscope mode, a guided measured image M2 is generated on the third path P3.

The spectrum obtaining/image acquiring unit 106 comprises a polarized light splitting unit 106a, a spectrum obtaining unit 106a and an image acquiring unit 106.

On the interference mode, the polarized light splitting unit 106a receives the interference image and; on the other hand, receives the measured image on the microscope mode to obtain a first to-be-analyzed image and a second to-be-analyzed image. The spectrum obtaining unit 106a receives the first to-be-analyzed image to generate a spectrum message. The image acquiring unit 106b receives the second to-be-analyzed image for use of subsequent analysis processing, so that a relationship between the second-to-be-analyzed image and the measured object A may be used to deduce some geometrical parameters of the measured object A.

The signal processing unit 107 is used to analyze and calculate several geometrical parameters of the measured object A. On the interference mode, the signal processing unit 107 controls the measured object A to move along a vertical direction V, and analyzes the second to-be-analyzed image, thereby securing a zero optical path difference for each of a plurality of pixels in the second to-be-analyzed image and records the zero optical path difference for each of the plurality of pixels in the second to-be-analyzed image, thereby enabling the spectrum obtaining unit 106a to obtain the spectrum message, thereby calculating a surface topography of the measured object A according to the spectrum message or the second to-be-analyzed image.

Further, the signal processing unit 107 closes the reference light aperture 102a to enable the optical measurement device 100 to enter the microscope mode, enabling the spectrum obtaining unit 106a to obtain a spectrum message when the zero optical path difference exists, activates the measured object A to move along the vertical direction V, analyzes a focal information of each of the plurality of pixels in the second to-be-analyzed image to obtain a full focal colorful image and a full focal gray-level image, and establishing a depth response curve.

Thereafter, the signal processing unit 107 further activates the measured object A to move laterally, to obtain a large-range surface profile according to the spectrum message, the depth response curve and a axial dispersion phenomenon.

Finally, when the zero optical path difference face exists, a bulk dimension and an another surface profile are deduced according to the spectrum message, wherein the surface profile is the another surface profile and the signal processing unit 107 selects to only calculate and present one of the surface profile and the another surface profile.

In the following, the optical measurement device 100 will be described for its more details in some preferred embodiments.

The reference light processing unit 104 further comprises an optical path difference precision shift mechanism 104a and a reference light reflector precision shift mechanism 104b. The mechanism 104a adjusts the collimated effect reference light to have a zero optical path difference with respect to the measured light, while the mechanism 104b adjusts a contrast of a plurality of interference strips in the interference image.

The polarized light splitting unit 106a further comprises an adjustment splitting angle rotational platform (not shown), for adjusting an image definition of the plurality of strips in the interference image.

The optical measurement device 100 of the present invention further comprises a measure object supporting mechanism 108, which comprises a piezoelectric activator 108a and an precision shift platform 108b, used for supporting the piezoelectric activator 108a. In the mechanism 10, the piezoelectric activator 108a is controlled by the signal processing unit 107 to move the measured object A along the vertical direction V on the interference mode, while the precision shift platform 108b is used to support the piezoelectric activator 108a.

The signal processing unit 1207 activates the measured object A to move along the vertical direction V on the microscope mode, analyzes a high frequency information of each of the plurality of pixels in the second measured image, matching a depth of field gray value of each of the plurality of pixels, restoring an image out-focal information to form the full focal colorful image and the full focal gray-level image, and establishing the depth response curve.

The signal processing unit 107 restores the image out-focal information to deduce the full focal gray-level image by using an image contrast filtering method and analyzed high frequency information of each of the plurality of pixels in the second measured image. Furthermore, the to-be-analyzed image is divided into three colors R, G and B images, and the three colors R, G and B images are then analyzed and overlapped to restore the full focal colorful image.

On the microscope mode, the spectrum obtaining unit 106 acquires a spectrum message of an upper surface of the substrate and an upper face of the coating layer, respectively, and reversely deduces a distance between the upper surface of the substrate and the upper face of the coating layer of the measured object A and serving the distance as a thickness of the coating layer.

The image acquiring unit 106b and the spectrum obtaining unit 106b are capable of detecting a visible light or a non-visible light.

The signal processing unit 107 applies a phase shift algorithm onto the plurality of interference stripes and analyzes a maximum strength of the plurality of interference stripes, so as to establish a surface profile information to acquire a surface profile of the measured object A.

Now, referring to FIG. 2, by which each of the units of the optical measurement device of the present invention is described with its further detailed elements accompanying with FIG. 1.

As shown, the light source unit 101 comprises a collimated light module 10 and a polarization plate 14. The collimated light module 10 comprises a doublet 11, a pinhole 12, and a focal lens 13. The polarization plate 14 comprises a polarization plate rotational platform 15. The reference light processing unit 104 comprises a reference light reflector 16 and an infinite calibration object lens 17. On a midway of the measured light M1 to the measured object supporting unit 108 (not shown in FIG. 2, but the one comprises the piezoelectric element activation unit 108a and the measured object supporting platform 108b), an infinite calibration unit 18 and a focal lens 19 are provided.

On a path between the polarized light splitting unit 106a to the spectrum obtaining unit 106b, a pinhole 20 and a focal lens 21 are provided. The polarized light splitting unit 106a further comprises a polarized light splitting unit rotational unit (not shown). On a path between the polarized light splitting unit 106a to the image acquiring unit 106c, a focal lens 22 is further comprised. Persons of the skilled arts may readily know how the detailed optical elements operate, and thus omitted herein for clarity.

By means of the above description, it may be known that the present invention is established by taking the Linnik interferometer as a basis, and integrating the functions provided by the conventional interferometer, microscope and ellipsometer. Namely, the surface profile measurement of the conventional white-light interferometer, the full depth of field image analysis of the microscope, and the layer thick measurement of the ellipsometer are totally integrated in function, and thus the three dimensional geometrical parameters such as the surface profile, full focal colorful and gray-level images, large-range surface profile, and bulk dimension.

As such, the advantages and efficacies of equipment cost saving, on-line measuring, rapid monitoring, reduced manufacturing time, and reduced possibility of object damage during the manufacturing process may be secured by the optical measurement device in the present invention, compared with the prior art.

Figure 3A:
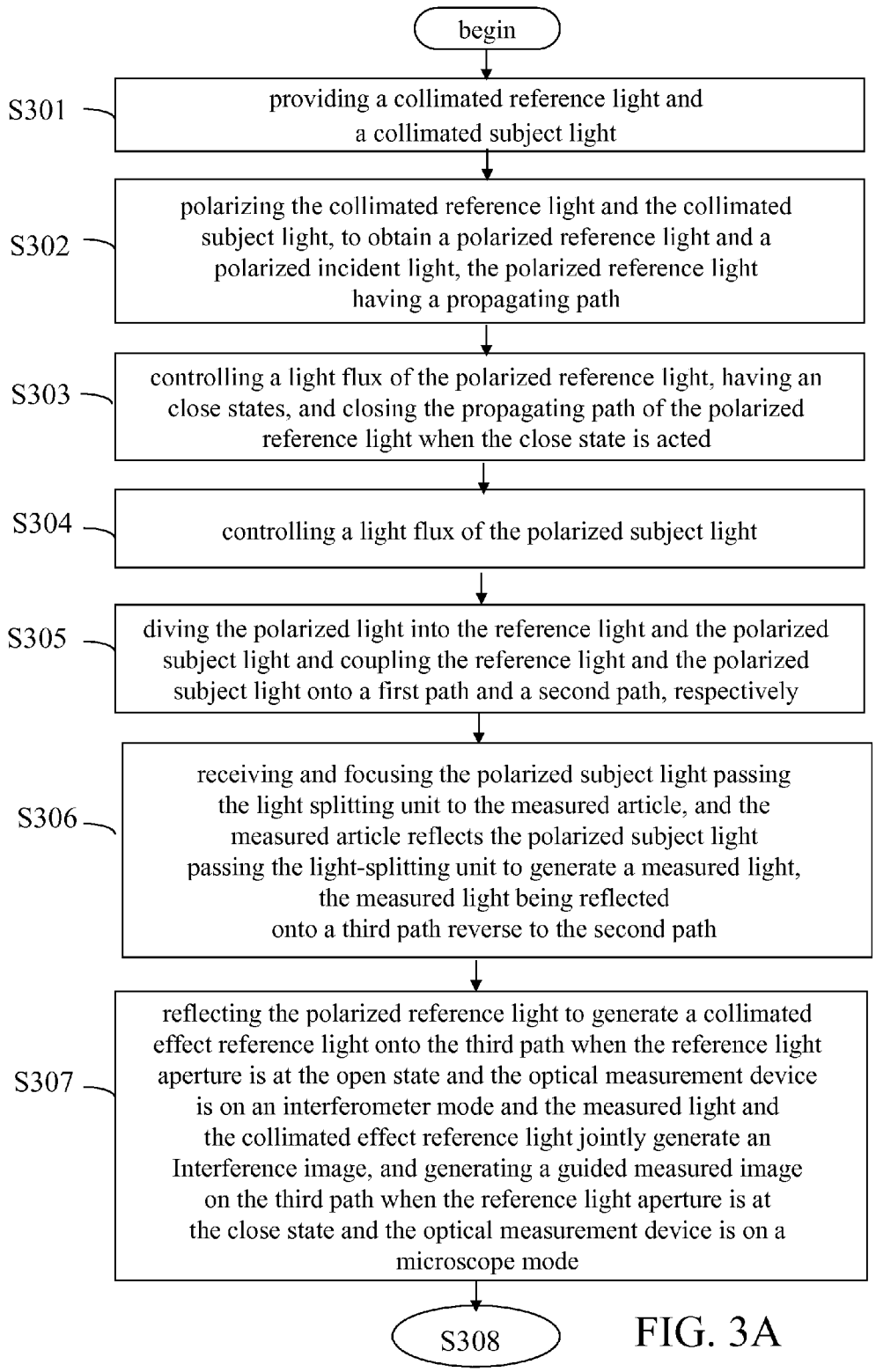
FIGS. 3A, 3B and 3C are jointly a flowchart of the method for optically measuring a plurality of parameters of an object according to the present invention.
Figure 3B:
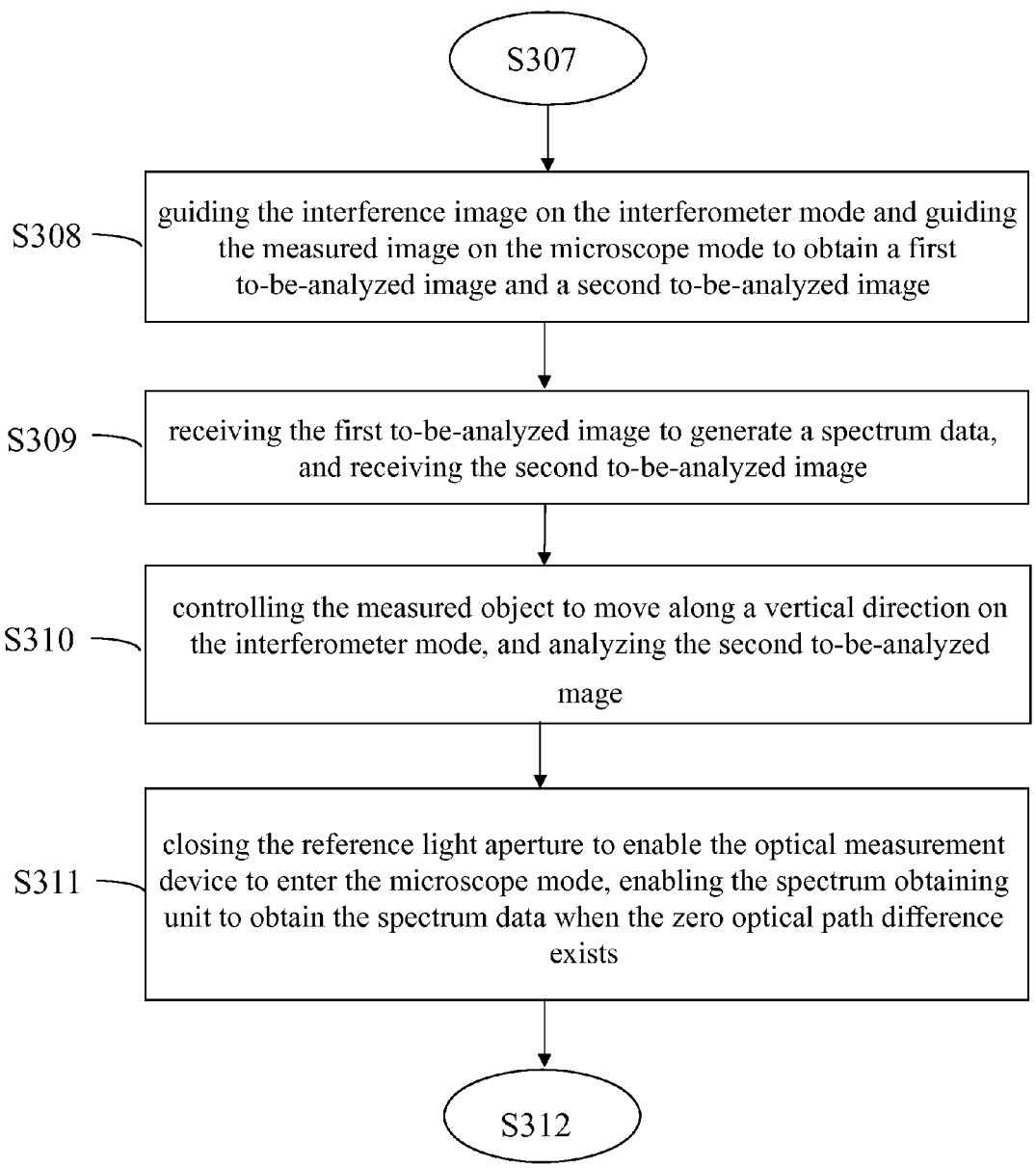
Figure 3C:
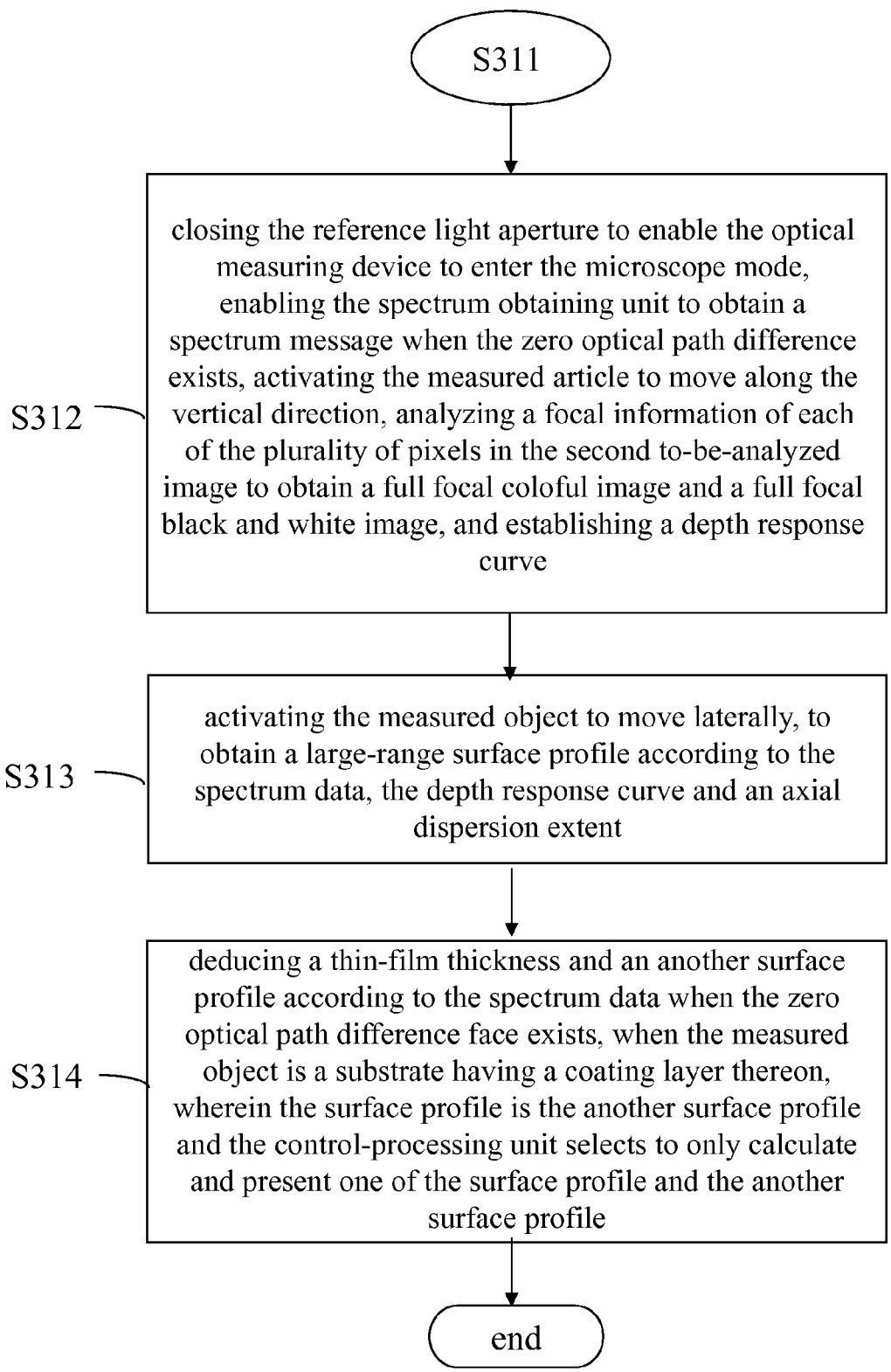

In the following, FIGS. 3A, 3B and 3C are jointly used to explain a flowchart of the method for optically measuring a plurality of parameters of an object according to the present invention.

In the method of the present invention, a collimated reference light and a collimated subject light are first provided (S301). Next, the collimated reference light and the collimated subject light are used to obtain a polarized reference light and a polarized subject light (S302), wherein the polarized reference light has a propagating path. Thereafter, a light flux of the polarized reference light, having an open and close states, is controlled and the propagating path of the polarized reference light is closed when the close state is acted (S303). Subsequently, a light flux of the polarized subject light is controlled (S304). Then, the polarized light into the reference light and the polarized subject light are dived and the reference light and the polarized subject light are coupled onto a first path and a second path, respectively (S305). Next, the polarized subject light is received and focused to the measured object, wherein the measured object reflects the polarized subject light passing the light-splitting unit to generate a measured light, and the measured light is reflected onto a third path reverse to the second path; (S306). Then, the polarized reference light is reflected to generate a collimated effect reference light onto the third path when the reference light aperture is at the open state and the optical measurement device is on an interferometer mode and the measured light and the collimated effect reference light jointly generate an interference image and a guided measured image is generated on the third path when the reference light aperture is at the close state and the optical measurement device is on a microscope mode (S307). Thereafter, the interference image is guided on the interferometer mode and the measured image is guided on the microscope mode to obtain a first to-be-analyzed image and a second to-be-analyzed image (S308). Thereafter, the first to-be-analyzed image is received to generate a spectrum data and the second to-be-analyzed image is received (S309). Then, the measured object is controlled to move along a vertical direction on the interferometer mode, and the second to-be-analyzed image is analyzed, thereby securing a zero optical path difference for each of a plurality of pixels in the second to-be-analyzed image and recording the zero optical path difference for each of the plurality of pixels in the second to-be-analyzed image, thereby enabling the spectrum obtaining unit to obtain the spectrum data, thereby calculating a surface topography of the measured object according to at least one of the spectrum data and the second to-be-analyzed image (S310). Thereafter, the reference light aperture is closed to enable the optical measurement device to enter the microscope mode, enabling the spectrum obtaining unit to obtain the spectrum data when the zero optical path difference exists (S311). Next, the measured object is activated to move along the vertical direction, a focal information of each of the plurality of pixels in the second to-be-analyzed image is analyzed to obtain a full focal colorful image and a full focal gray-level image, and establishing a depth response curve (S312). Thereafter, the measured object is activated to move laterally, to obtain a large-range surface profile according to the spectrum data, the depth response curve and an axial dispersion extent (S313). Finally, a thin-film thickness and an another surface profile are deduced according to the spectrum data when the zero optical path difference face exists, when the measured object is a substrate having a coating layer thereon, wherein the surface profile is the another surface profile and the control-processing unit selects to only calculate and present one of the surface profile and the another surface profile (S314).

For the further detailed description for the optical measurement method of the present invention, it may be referred to the corresponding part in the above description for the optical measurement device of the present invention, and omitted herein for clarity.

As compared to the prior art methods, the optical measurement method has its advantages and efficacies, which are similar to what are described for the optical measurement device of the present invention and may be known by directly referring to the related description in the above and omitted herein for clarity.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:
1. An optically measurement device for measuring a plurality of parameters, comprising:
   a light source unit, comprising:
      an external light source;
      a collimation unit, coupling the external light source to provide a collimated reference light and a collimated subject light; and
      a polarizer unit, polarizing the collimated reference light and the collimated subject light, to obtain a polarized reference light and a polarized subject light, the polarized reference light propagating on a propagating path;
   an aperture unit, comprising a reference light aperture, controlling a light flux of the polarized reference light, having an open and close states, and closing the propagating path of the polarized reference light when the close state is acted;
   an incident light aperture, controlling a light flux of the polarized subject light; and a measured light aperture;
   a light splitting unit, diving the polarized light into the reference light and the polarized subject light and coupling the reference light and the polarized subject light onto a first path and a second path, respectively;
   a measured end unit, locating on the second path, receiving and focusing the polarized subject light to the measured object, the measured object reflecting the polarized subject light passing the light-splitting unit to generate a measured light, the measured light being reflected onto a third path reverse to the second path;
   a reference light processing unit, locating on the first path, and reflecting the polarized reference light to generate a collimated effect reference light onto the third path when the reference light aperture is at the open state and the optical measurement device is on an interferometer mode and the measured light and the collimated effect reference light jointly generate an interference image through the light-splitting unit, and generating a guided measured image on the third path when the reference light aperture is at the close state and the optical measurement device is on a microscope mode;
   a spectrum obtaining/image acquiring unit, comprising a polarized light splitting unit, guiding the interference image on the interferometer mode and guiding the measured image on the microscope mode to obtain a first to-be-analyzed image and a second to-be-analyzed image;
   a spectrum obtaining unit, receiving the first to-be-analyzed image to generate a spectrum data; and an image acquiring unit, receiving the second to-be-analyzed image; and
   a control-processing unit, performing steps of:
      controlling the measured object to move along a vertical direction on the interferometer mode, and analyzing the second to-be-analyzed image, thereby securing a zero optical path difference for each of a plurality of pixels in the second to-be-analyzed image and recording the zero optical path difference for each of the plurality of pixels in the second to-be-analyzed image, thereby enabling the spectrum obtaining unit to obtain the spectrum data, thereby calculating a surface topography of the measured object according to at least one of the spectrum data and the second to-be-analyzed image;
      closing the reference light aperture to enable the optical measurement device to enter the microscope mode, enabling the spectrum obtaining unit to obtain the spectrum data when the zero optical path difference exists;
      activating the measured object to move along the vertical direction, analyzing a focal information of each of the plurality of pixels in the second to-be-analyzed image to obtain a full focal colorful image and a full focal gray-level image, and establishing a depth response curve;

activating the measured object to move laterally, to obtain a large-range surface profile according to the spectrum data, the depth response curve and an axial dispersion extent; and deducing a thin-film thickness and an another surface profile according to the spectrum data when the zero optical path difference face exists, when the measured object is a substrate having a coating layer thereon, wherein the surface profile is the another surface profile and the control-processing unit selects to only calculate and present one of the surface profile and the another surface profile.

2. The optically measurement device as claimed in claim 1, wherein:

the reference light processing unit further comprises:
an optical path difference precision shift mechanism, used for adjusting the collimated effect reference light, so that the collimated effect reference light has a zero path difference with respect to the measured light; and
a reference light reflector precision shift mechanism, used for adjusting a contrast of a plurality of interference stripes in the interference image;

the polarized light splitting unit further comprises a splitter angle adjustment rotation platform, used for adjusting an image definition of the plurality of interference stripes in the interference image; and the optical measurement device further comprises a measured object supporting mechanism, comprising:
a piezoelectric activator, being controlled by the signal processing unit to move the measured object along the vertical direction on the interference mode; and
an precision shift platform, used for supporting the piezoelectric activator.

3. The optically measurement device as claimed in claim 1, wherein the signal processing unit activates the measured object to move along the vertical direction on the microscope mode, analyzing a high frequency information of each of the plurality of pixels in the second measured image, matching a depth of field gray value of each of the plurality of pixels, restoring an image out-focal information to form the full focal colorful image and the full focal gray-level image, and establishing the depth response curve.

4. The optically measurement device as claimed in claim 3, wherein the signal processing unit restores the image out-focal information to deduce the full focal gray-level image by using an image contrast filtering method and analyzed high frequency information of each of the plurality of pixels in the second measured image.

5. The optically measurement device as claimed in claim 1, wherein the spectrum obtaining unit acquires a spectrum message of an upper surface of the substrate and an upper face of the coating layer, respectively, and reversely deduces a distance between the upper surface of the substrate and the upper face of the coating layer of the measured object and serving the distance as a thickness of the coating layer.

6. The optically measurement device as claimed in claim 1, wherein the external light source is one of a white-light halogen lamp and an infrared lamp and has a Gaussian distributed intensity.

7. The optically measurement device as claimed in claim 1, wherein the image acquiring unit is capable of detecting one of a visible light and a non-visible light.

8. The optically measurement device as claimed in claim 1, wherein the signal processing unit applies a phase shift algorithm onto the plurality of interference stripes and analyzes a maximum strength of the plurality of interference stripes, so as to establish a surface profile information to acquire a surface profile of the measured object.

9. A method for optically measuring a plurality of parameters of an object, comprising steps of:

(a) providing a collimated reference light and a collimated subject light;

(b) polarizing the collimated reference light and the collimated subject light, to obtain a polarized reference light and a polarized subject light, the polarized reference light having a propagating path;

(c) controlling a light flux of the polarized reference light, having an open and close states, and closing the propagating path of the polarized reference light when the close state is acted;

(d) controlling a light flux of the polarized subject light;

(e) diving the polarized light into the reference light and the polarized subject light and coupling the reference light and the polarized subject light onto a first path and a second path, respectively;

(f) receiving and focusing the polarized subject light to the measured object, the measured object reflecting the polarized subject light passing the light-splitting unit to generate a measured light, the measured light being reflected onto a third path reverse to the second path;

(g) reflecting the polarized reference light to generate a collimated effect reference light onto the third path when the reference light aperture is at the open state and the optical measurement device is on an interferometer mode and the measured light and the collimated effect reference light jointly generate an interference image, and generating a guided measured image on the third path when the reference light aperture is at the close state and the optical measurement device is on a microscope mode;

(h) guiding the interference image on the interferometer mode and guiding the measured image on the microscope mode to obtain a first to-be-analyzed image and a second to-be-analyzed image;

(i) receiving the first to-be-analyzed image to generate a spectrum data, and receiving the second to-be-analyzed image;

(j) controlling the measured object to move along a vertical direction on the interferometer mode, and analyzing the second to-be-analyzed image, thereby securing a zero optical path difference for each of a plurality of pixels in the second to-be-analyzed image and recording the zero optical path difference for each of the plurality of pixels in the second to-be-analyzed image, thereby enabling the spectrum obtaining unit to obtain the spectrum data, thereby calculating a surface topography of the measured object according to at least one of the spectrum data and the second to-be-analyzed image;

(k) closing the reference light aperture to enable the optical measurement device to enter the microscope mode, enabling the spectrum obtaining unit to obtain the spectrum data when the zero optical path difference exists;

(l) activating the measured object to move along the vertical direction, analyzing a focal information of each of the plurality of pixels in the second to-be-analyzed image to obtain a full focal colorful image and a full focal gray-level image, and establishing a depth response curve;

(m) activating the measured object to move laterally, to obtain a large-range surface profile according to the spectrum data, the depth response curve and an axial dispersion extent; and (n) deducing a thin-film thickness and an another surface profile according to the spectrum data when the zero optical path difference face exists, when the measured object is a substrate having a coating layer thereon, wherein the surface profile is the another surface profile and the control-processing unit selects to only calculate and present one of the surface profile and the another surface profile.

10. The optically measurement device as claimed in claim 9, wherein: extent the step (c) further comprises a step of:
   (c1) adjusting the collimated effect reference light, so that the collimated effect reference light has a zero path difference with respect to the measured light;
the step (e) further comprises steps of:
   (e1) adjusting a contrast of a plurality of interference stripes in the interference image; and
   (e2) adjusting an image definition of the plurality of interference stripes in the interference image; and
the method further comprises a step prior to the step (a) of:
   (a1) supporting the piezoelectric activator and controlling the measured object to move along the vertical direction on the interference mode.

11. The method as claimed in claim 9, wherein the step (l) further comprises a step of:
   (l1) analyzing a high frequency information of each of the plurality of pixels in the second measured image, matching a depth of field gray value of each of the plurality of pixels, restoring an image out-focal information to form the full focal colorful image and the full focal gray-level image, and establishing the depth response curve.

12. The method as claimed in claim 11, wherein the step (l1) further comprises a step of:
   (l2) restoring the image out-focal information to deduce the full focal gray-level image by using an image contrast filtering method and analyzed high frequency information of each of the plurality of pixels in the second measured image.

13. The method as claimed in claim 9, wherein the step (n) further comprises a step of:
   (n1) acquiring a spectrum message of an upper surface of the substrate and an upper face of the coating layer, respectively, and reversely deduces a distance between the upper surface of the substrate and the upper face of the coating layer of the measured object and serving the distance as a thickness of the coating layer.

14. The method as claimed in claim 9, wherein the collimated reference light is one of a white-light halogen lamp and an infrared lamp and has a Gaussian distributed intensity.

15. The method as claimed in claim 9, wherein the image acquiring unit is capable of detecting one of a visible light and a non-visible light.

16. The method as claimed in claim 9, wherein the step (k) further comprises a step of:
   (k1) applying a phase shift algorithm onto the plurality of interference stripes and analyzes a maximum strength of the plurality of interference stripes, so as to establish a surface profile information to acquire a surface profile of the measured object.

* * * * *